(12) United States Patent
Huynh et al.

(10) Patent No.: US 9,664,661 B2
(45) Date of Patent: May 30, 2017

(54) OLFACTORY APPLICATION CONTROLLER INTEGRATED CIRCUIT

(71) Applicant: Active-Semi, Inc., Tortola (VG)

(72) Inventors: Steven Huynh, Fremont, CA (US); XuCheng Wang, Guangdong (CN)

(73) Assignee: Active-Semi, Inc. (VG)

( * ) Notice: Subject to any disclaimer, the term of this patent is extended or adjusted under 35 U.S.C. 154(b) by 99 days.

(21) Appl. No.: 14/697,543

(22) Filed: Apr. 27, 2015

(65) Prior Publication Data

US 2015/0323510 A1 Nov. 12, 2015

Related U.S. Application Data (60) Provisional application No. 61/990,705, filed on May 8, 2014.

(51) Int. Cl.
| | | |
|---|---|---|
| *G01N 7/00* | (2006.01) | |
| *G01N 33/497* | (2006.01) | |
| *G01N 33/00* | (2006.01) | |
| *H01L 23/29* | (2006.01) | |
| *H01L 23/31* | (2006.01) | |

(52) U.S. Cl.
CPC ..... *G01N 33/0031* (2013.01); *G01N 33/0001* (2013.01); *H01L 23/293* (2013.01); *H01L 23/3157* (2013.01); *H01L 23/3107* (2013.01); *H01L 2224/48091* (2013.01); *H01L 2224/48137* (2013.01); *H01L 2224/49171* (2013.01); *H01L 2224/49175* (2013.01)

(58) Field of Classification Search
USPC ................... 73/23.34, 23.4, 23.42
See application file for complete search history.

(56) References Cited

U.S. PATENT DOCUMENTS

| | | | | |
|---|---|---|---|---|
| 3,428,892 A | * | 2/1969 | Meinhard ............ | G01N 27/126 252/500 |
| 3,464,799 A | * | 9/1969 | Kimbell ............. | G01N 21/8483 422/91 |
| 6,598,459 B1 | * | 7/2003 | Fu ...................... | G01N 33/0031 73/23.34 |

(Continued)

*Primary Examiner* — Clayton E Laballe
*Assistant Examiner* — Warren K Fenwick
(74) *Attorney, Agent, or Firm* — Imperium Patent Works; Amir V. Adibi; Daniel D. Tagliaferr (57) ABSTRACT

An integrated circuit that senses ambient gas concentrations includes a microcontroller, gas sensors, heating resistors and an analog-to-digital converter. A first gas sensor measures a first attribute of a gas concentration, and a second gas sensor measures a second attribute of the gas concentration. The first attribute varies with the gas concentration differently than does the second attribute. The microcontroller controls the duty cycles of signals driven through the heating resistors to adjust the temperatures of the resistors, which are thermally coupled to the gas sensors. A first heating resistor increases the temperature of the first gas sensor to a first target temperature, and a second heating resistor increases the temperature of the second gas sensor to a second target temperature. The analog-to-digital converter converts the attributes measured by the first and second gas sensors into digital values. The microcontroller then uses the digital values to compute the gas concentration.

20 Claims, 7 Drawing Sheets

OLFACTORY APPLICATION CONTROLLER IC SCHEMATIC DIAGRAM (56) References Cited

U.S. PATENT DOCUMENTS

| | | | |
|---|---|---|---|
| 7,905,154 B2* | 3/2011 | Jones, Jr. | A22B 5/007 |
| | | | 73/23.34 |
| 8,220,310 B2* | 7/2012 | Yamanaka | G01N 29/022 |
| | | | 73/23.4 |
| 8,852,946 B2* | 10/2014 | Lee | G01N 33/0031 |
| | | | 252/372 |
| 2004/0016287 A1* | 1/2004 | Fu | G01N 33/0031 |
| | | | 73/23.34 |
| 2014/0311217 A1* | 10/2014 | Lee | G01N 33/0009 |
| | | | 73/23.34 |
| 2015/0168327 A1* | 6/2015 | Dimmler | G01N 27/4148 |
| | | | 73/23.4 |
| 2015/0308993 A1* | 10/2015 | Fukui | G01N 33/0034 |
| | | | 73/23.34 |
| 2015/0308996 A1* | 10/2015 | Kim | G01N 33/0001 |
| | | | 73/23.34 |
| 2015/0308999 A1* | 10/2015 | Villareal Guerra | G01N 33/0031 |
| | | | 73/23.34 |

* cited by examiner

OLFACTORY APPLICATION CONTROLLER IC SCHEMATIC DIAGRAM

FIG. 1

SENSOR ARRAY DIE EMBODIMENT

FIG. 2

ENCAPSULATED OACIC EMBODIMENT

FIG. 3

OAC MIXED-SIGNAL DIE SCHEMATIC DIAGRAM

ENCAPSULATED OACIC MONOLITHIC EMBODIMENT

FIG. 7

OLFACTORY APPLICATION CONTROLLER INTEGRATED CIRCUIT

CROSS REFERENCE TO RELATED APPLICATION

This application claims the benefit under 35 U.S.C. §119 of U.S. Provisional Application Ser. No. 61/990,705, entitled "Olfactory Application Controller Integrated Circuit," filed on May 8, 2014, the subject matter of which is incorporated herein by reference.

TECHNICAL FIELD

The described embodiments relate generally to sensor circuits and more specifically to an integrated circuit that senses the concentrations of various gasses in the air.

BACKGROUND INFORMATION

Multiple applications exist for devices that can mimic the function of the human nose to detect different molecules in the air. The present invention describes embodiments of an Olfactory Application Controller Integrated Circuit (OACIC), together with methods for measuring gas concentrations using the OACIC and methods for factory calibration of the OACIC.

SUMMARY

An integrated circuit that senses gas concentrations in the surrounding air includes a microcontroller, gas sensors, heating resistors, an analog-to-digital converter and a communication circuit. The heating resistors are thermally coupled to the gas sensors. A first gas sensor measures a first attribute of a gas concentration, and a second gas sensor measures a second attribute of the gas concentration. The first attribute varies with the gas concentration differently than does the second attribute. The microcontroller controls the duty cycles of signals driven through the heating resistors to adjust the temperatures of the heating resistors. A first heating resistor increases the temperature of the first gas sensor to a first target temperature, and a second heating resistor increases the temperature of the second gas sensor to a second target temperature. The analog-to-digital converter converts the attributes measured by the first and second gas sensors into digital values. The microcontroller then uses the digital values to compute the gas concentration. The communication circuit outputs information indicative of the gas concentration.

In embodiments of the present invention, an integrated circuit is adapted for measuring a gas concentration. The integrated circuit comprises a microcontroller, a nonvolatile memory, a set of at least two gas sensors, a set of heating resistors, an analog-to-digital converter, and a communication circuit. The gas sensors are exposed to air. Each gas sensor has an attribute that has a different sensitivity to the gas concentration. Each heating resistor is associated with a gas sensor and raises the temperature of the associated gas sensor to a target temperature above the ambient temperature. The analog-to-digital converter is operable to convert the attributes of the gas sensors into digital values. The digital values corresponding to at least two gas sensors are used by the microcontroller to compute the gas concentration. At least two gas sensors are differentially sensitive to the gas concentration. The communication circuit is operable to communicate the gas concentration information out of the integrated circuit. A drive signal for each heating resistor has a pulse-width-modulation duty cycle that is controlled by the microcontroller to set the heating resistor to a target temperature. The integrated circuit further comprises a humidity sensor and an ambient temperature sensor. Information from the humidity sensor and the ambient temperature sensor is used in computing the gas concentration. In an exemplary embodiment, the integrated circuit is field programmable. The integrated circuit has nonvolatile memory that stores sensor calibration parameters, and pattern recognition weight matrices that compute the gas concentration. The integrated circuit is encapsulated in a plastic package with an opening for gas molecules to enter and interact with the gas sensors. The integrated circuit may drive the heating resistors in conditions where it has not detected an abnormal gas concentration or humidity in the air. The integrated circuit computes the gas concentration with data from at least one gas sensor at two different heating temperatures. In an exemplary embodiment, the integrated circuit further comprises an auto-scan circuit that sequentially converts the attributes of the gas sensors into digital values and stores the digital values into a result register.

In other embodiments of the present invention, an integrated circuit is disclosed for sensing a gas concentration from a sensor array that includes at least two gas sensors and associated heating resistors. The sensor array is exposed to the air. Each heating resistor raises the temperature of the corresponding gas sensor. Each gas sensor has an attribute that has a different sensitivity to the gas concentration. In an exemplary embodiment, the integrated circuit comprises a microcontroller, a nonvolatile memory, a first set of terminals, a second set of terminals, a set of drivers, a multiplexer, an analog-to-digital converter, and a digital comparator. The first set of terminals is coupled to the heating resistors, and the second set of terminals is coupled to the gas sensors. The set of drivers is operable to drive the heating resistors with a drive signal through the first set of terminals. The drive signal of each heating resistor has a duty cycle that is controlled to set the heating resistor to a target temperature. The multiplexer is operable to select a sensor signal from among a set of sensor signals that are received on conductors coupled to the second set of terminals. The analog-to-digital converter converts the selected sensor signal into a digital value that is used by the controller to compute the gas concentration. The integrated circuit and the sensor array are encapsulated in an integrated circuit package. The integrated circuit has an opening for gas molecules to enter and interact with the gas sensors. At least one gas sensor uses a metal oxide semiconductor sensitive layer for gas sensing. The heating resistors are also used for temperature sensing. The digital comparator compares the digital values to alarm thresholds. The comparing results in an alarm signal if the gas concentration is abnormal (and/or outside the thresholds).

A method for measuring gas concentrations in a sampling cycle involves setting duty cycles, terminating heating, initiating an auto-scan sequence, calibrating sensor data, calibrating temperature data, compensating the sensor data and the temperature data, computing gas concentrations, determining a sampling cycle delay, and beginning the next sampling cycle. Duty cycles are set for a pulse-width-modulation generator to generate drive signals to heat sensors in a sensor array to target temperatures. After a heating delay time, the heating is terminated and an auto-scan sequence is initiated that converts the sensor and temperature signals from the sensor array into sensor data and temperature data. The sensor data is calibrated with sensor calibration parameters, and the temperature data is calibrated with heater calibration parameters in a nonvolatile memory. The sensor data and the temperature data is compensated with drift compensation parameters based on sensor aging data. Gas concentrations are computed based on pattern recognition weight matrices in the nonvolatile memory. The sampling cycle delay is determined based on the gas concentrations. The next sampling cycle is begun after the sampling cycle delay.

A method for mass producing an integrated circuit involves performing electrical testing on the integrated circuit, subjecting the integrated circuit to different gas concentrations, reading sensor and temperature data, calculating sensor calibration parameters, calculating heater calibration parameters, programming the calibration parameters, and programming drift compensation parameters and pattern recognition weight matrices. The integrated circuit is subjected to a series of different gas molecular concentrations at target test temperatures in environmental test equipment. Sensor data and temperature data is read in the integrated circuit. Sensor calibration parameters are calculated from the sensor data to match gas concentration measurement data from reference instruments. Heater calibration parameters are calculated from the temperature data to match temperature measurement data from reference instruments. The sensor calibration parameters and the heater calibration parameters are programmed into the nonvolatile memory of the integrated circuit. Drift compensation parameters and pattern recognition weight matrices are programmed into the nonvolatile memory of the integrated circuit.

Further details and embodiments and techniques are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

DETAILED DESCRIPTION

Reference will now be made in detail to background examples and some embodiments of the invention, examples of which are illustrated in the accompanying drawings.

Figure 1:
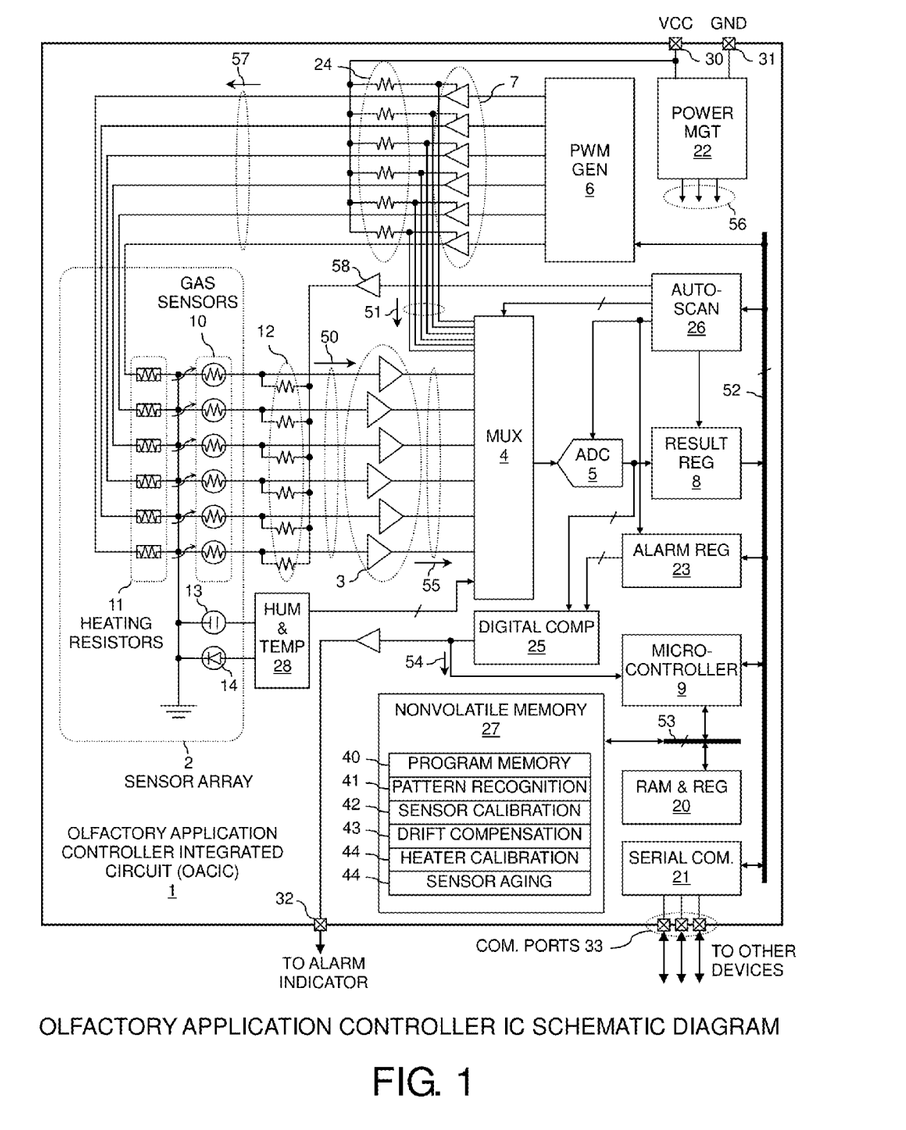
FIG. 1 is an exemplary schematic diagram of an Olfactory Application Controller Integrated Circuit (OACIC).

FIG. 1 is an exemplary schematic diagram of an Olfactory Application Controller Integrated Circuit (OACIC) 1. In an exemplary embodiment, the OACIC is a field-programmable device. The OACIC 1 comprises a sensor array 2, amplifiers 3, a multiplexer 4, an analog-to-digital converter (ADC) 5, a pulse-width-modulation (PWM) generator 6, heater drivers 7, a result register 8, a microcontroller 9, a nonvolatile memory 27, a humidity and temperature converter 28, a random-access memory (RAM) and register 20, a digital comparator 25, an alarm register 23, an auto-scan circuit 26, a serial communication circuit 21, and a power management circuit 22. The sensor array 2 includes gas sensors 10 and associated heating resistors 11, a humidity sensor 13, and an ambient temperature sensor 14. The OACIC 1 further includes a VCC supply port 30, a GND ground port 31, communication ports 33, and an alarm indicator port 32. In an exemplary embodiment, the sensor array 2 is disposed on a micro-machined die, while the rest of the circuitry in the OACIC 1 is on a separate mixed signal die. In another embodiment, the sensor array 2 is part of one monolithic OACIC die. The OACIC 1 is encapsulated in an integrated package with a gas sensing opening for the gas sensors 10, a humidity sensor 13, and an ambient temperature sensor 14 in sensor array 2.

The OACIC 1 senses the environment with gas sensors 10 in the sensor array 2. The number of gas sensors in sensory array 2 typically ranges from 2 to 40. The gas sensors 10 are differentially sensitive to different types of gas molecules. In the preferred embodiment, each sensor among gas sensors 10 includes a different sensitive material that varies differentially in resistivity when exposed to different target molecules, such as oxygen ($O_2$), carbon dioxide ($CO_2$), carbon monoxide (CO), methane ($CH_4$), nitrogen dioxide ($NO_2$), formaldehyde ($CH_2O$), radon, and other gases. Such sensitive materials are typically metal oxide semiconductor (MOX) materials. The specific sensitive materials include, but are not limited to, metal oxides such as tin oxide ($SnO_2$), titanium oxide ($TiO_2$), tungsten oxide ($WO_3$), zinc oxide (ZnO), with additional doping of other materials such as platinum (Pt). Each of the gas sensors 10 typically ranges in resistance from 1 kilo-ohm to 500 kilo-ohm, and typically varies by a more than a factor of 2 in resistance when exposed to a high concentration of the target molecules. Differential resistance of at least two gas sensors is used to determine a gas concentration. Each of the gas sensors 10 have typical dimensions ranging from 100 micro-meters to 1000 micro-meters each, and have a sensitive material thickness typically ranging from 50 nanometers to 500 nanometers. Each of the gas sensors 10 is heated exclusively by the associated heating resistor among the heating resistors 11, with heating temperatures typically ranging up to a maximum 450 degrees Celsius. The heating resistors 11 are typically made of poly-silicon, platinum (Pt), or another material, beneath their associated gas sensors 10. Each of the heating resistors 11 typically ranges from 50 to 500 ohms in resistance, and typically dissipates from 10 to 100 milliwatts in heating power to bring its associated sensor to the maximum temperature. When driven by sensor driver 58 with bias resistors 12, sensor array 2 outputs sensor signals 50, which are amplified by amplifiers 3 to generate amplified sensor signals 55. PWM generator 6 controls the heater drivers 7 to provide PWM heater drive signals 57 to heating resistors 11. The PWM heater drive signals 57 have voltage amplitudes essentially equal to the supply voltage from the VCC supply port 30 of the OACIC 1. In an exemplary embodiment, the heater current sense signals 51 across driver current sense resistors 24 are proportional to the magnitudes of the currents flowing through heating resistors 11. The heater current sense signals 51 exhibit temperature coefficients related to the material composition of the heating resistors 11. The heater current sense signals 51 are used by the OACIC 1 to monitor the temperatures at each of the heating resistors 11. In other embodiments, the sensor array 2 may include separate heating resistors and heater temperature sensors.

Sensor array 2 includes humidity sensor 13 and ambient temperature sensor 14. Humidity and temperature converter 28 provides biasing and controlling signals to humidity sensor 13 and ambient temperature sensor 14. Humidity and temperature converter 28 converts humidity and temperature measurements into voltage signals and sends them through multiplexer 4 for conversion into digital values. The humidity sensor uses capacitance measurements of the polymer membrane to determine relative humidity, such as 10 millivolts per relative humidity percentage (% RH), while the ambient temperature sensor uses two different current biases to generate a voltage proportional to absolute temperature, such as 2 millivolts per degree Celsius. The accuracy of metal oxide semiconductor (MOX) sensors is affected by ambient humidity and temperature. The OACIC 1 integrates the ambient humidity and temperature sensors to allow the gas concentration computation algorithm to calibrate the readings with humidity and temperature data.

The multiplexer 4 is operable to be controlled by the auto-scan circuit 26 to sequentially select one analog signal from among the amplified sensor signals 55, the heater current sense signals 51, or signals from the humidity and temperature converter 28 and to couple those signals to the analog-to-digital converter (ADC) 5. ADC 5 performs conversion of the analog signal from multiplexer 4 into a digital signal value that is stored in the result register 8. The microcontroller 9 reads the result register 8 to determine the resistance (or another attribute) of each sensor or heating resistor in the sensor array 2.

With the information derived from the heater current sense signals 51, the microcontroller 9 determines the approximate temperature of each sensor in the sensor array 2 and configures the corresponding register in the PWM generator 6 accordingly in order to adjust the temperature of each sensor to a target temperature. The heater drivers 7 provide pulse-width-modulated voltage pulses to the heating resistors in the sensor array 2. If the temperature of a sensor is lower than the target temperature, the microprocessor 9 increases the PWM duty cycle of the corresponding heater driver. If the temperature of a sensor is higher than the target temperature, then microprocessor 9 decreases the PWM duty cycle of the corresponding heater driver. The heater drivers 7 receive supply power from the VCC supply port 30 so that the currents driving the heating resistors 11 do not dissipate power inside the OACIC 1.

The OACIC 1 includes nonvolatile memory 27 that stores program memory 40, pattern recognition weight matrices 41, sensor calibration parameters 42, drift compensation parameters 43, heater calibration parameters 44, and sensor aging data 44. During factory manufacturing of the OACIC 1, gas sensors 10 are calibrated with reference instruments and equipment for target molecules, and the parameters used to enable calibrated computational results from the sensor signals 50 are stored as sensor calibration parameters 42 in nonvolatile memory 27. During manufacturing of the OACIC 1, heating resistors 11 are calibrated with reference instruments and equipment for target temperatures. The parameters used to enable calibrated computational results from the heater current sense signals 51 are stored as heater calibration parameters 44 in nonvolatile memory 27. Drift compensation parameters 43 are also programmed during manufacturing of the OACIC 1 to enable drift compensation that reduces variations in computational results from the sensor signals 50 and heater current sense signals 51 over the useful lifetime of the OACIC 1. The OACIC 1 stores sensor aging data 44 of the lifetime heating profile of the gas sensors 10, which is used for drift compensation computations.

During factory manufacturing or field programming of the OACIC 1, pattern recognition weight matrices 41 are stored in nonvolatile memory 27. Multiple algorithms can be used for pattern recognition learning from multidimensional data from the sensor signals 50 and their associated temperatures, including principal component analysis (PCA), linear discriminant analysis (LDA), artificial neural networks (ANN), support vector machine (SVM), or other dimensionality reduction methods. The computational matrices resulting from pattern recognition learning algorithms are stored as pattern recognition weight matrices 41. During sensing operations, the OACIC 1 executes a program in the program memory 40, which reads data from the result register 8. The data read from the result register 8 includes ADC converted data from the sensor signals 50 and their associated temperatures. Executing the program performs calibrations and drift compensation and computes the gas concentration results using pattern recognition weight matrices 41. The computational algorithm relies on the differential sensitivity among gas sensors 10 to different types of gas molecules, and computes each gas concentration result based on the differential sensitivity to the gas concentration of at least two gas sensors in the sensor array 2. For example, a first gas sensor may be more sensitive to one gas concentration while a second gas sensor is not, and the computational algorithm relies on the larger change in the first gas sensor resistance and smaller change in the second gas sensor resistance to determine the gas concentration. The gas concentration results are communicated to other devices external to the OACIC 1 through the serial communication circuit 21 and communication ports 33. The computational algorithm also uses humidity and ambient temperature data to adjust the gas concentration measurements.

The power management circuit 22 in the OACIC 1 provides internal power supplies 56 to the different circuitry blocks except not to the heater drivers 7. In one example, the power management circuit 22, which comprises linear regulators, receives a 3.3 volt supply from VCC supply port 30, and generates a regulated 1.2 volt supply for the microcontroller 9 and a regulated 2.5 volt supply for the ADC 5. Even though much of the circuitry in OACIC 1 uses the lower regulated supply voltages, the heater drivers 7 use the VCC supply port 30 directly to drive the heating resistors 11 with 3.3 volt at a PWM duty cycle to minimize power loss in the OACIC 1 due to sensor heating.

The auto-scan circuit 26 in the OACIC 1 performs automatic sequencing using the multiplexer 4, sampling using the ADC 5, and storing the amplified sensor signals 55 and heater current sense signals 51 in the result register 8. For each data collection cycle, the microcontroller 9 first provides control information to the PWM generator 6 to bring the gas sensors 10 to their target temperatures, then activates the auto-scan circuit 26 to collect the data samples. The heater temperature values derived from the heater current sense signals 51 are then used to regulate the PWM generator 6 settings so that the temperatures of gas sensors 10 are closer to their target temperatures at the next data collection cycle.

The OACIC 1 field programmability allows different field configurable protection mechanisms to shut off the heaters due to sudden and abnormal high gas concentration to stop chemical reactions that may cause irreversible damage to the sensing surfaces. This can be achieved with both firmware detection of computed gas concentration levels in the OACIC 1 and with digital comparator 25. The OACIC 1 includes a digital comparator 25 that compares the ADC 5 result to the alarm register 23 during auto-scan sequencing. If the ADC 5 result is outside of the range specified by the alarm register 23 for any sensor, then the digital comparator issues an alarm signal 54 to the microcontroller 9 and to the alarm indicator port 32. This mechanism allows a quick response to abnormal gas concentration changes based on thresholds set by the microcontroller 9, including interrupting the microcontroller 9 so that it can disable the heater drivers 7 by discontinuing the PWM generator 6 when a gas concentration is high and has potential to permanently affect the sensing material. The alarm signal 54 can be used to drive an alarm buzzer to indicate a dangerous environmental condition. In an exemplary embodiment, the digital comparator 25 alarm mechanism can be operational even when the microcontroller 9 is powered down or in deep sleep mode, in which case the alarm signal 54 can be used to wake up the microcontroller 9 from the deep sleep mode to service the abnormal environmental condition.

The OACIC 1 computes gas concentration results from the data collected in the result register 8 using pattern recognition, calibration, and compensation parameters in nonvolatile memory 27. The OACIC 1 stores its computational results in its random-access memory (RAM) and register 20. The computational results are communicated to other devices through the communication ports 33 by the serial communication circuit 21. Serial communication circuit 21 uses a serial communication protocol such as SPI, I²C, UART, or USB. During serial communication, the OACIC 1 can be either a master device or a slave device.

Figure 2:
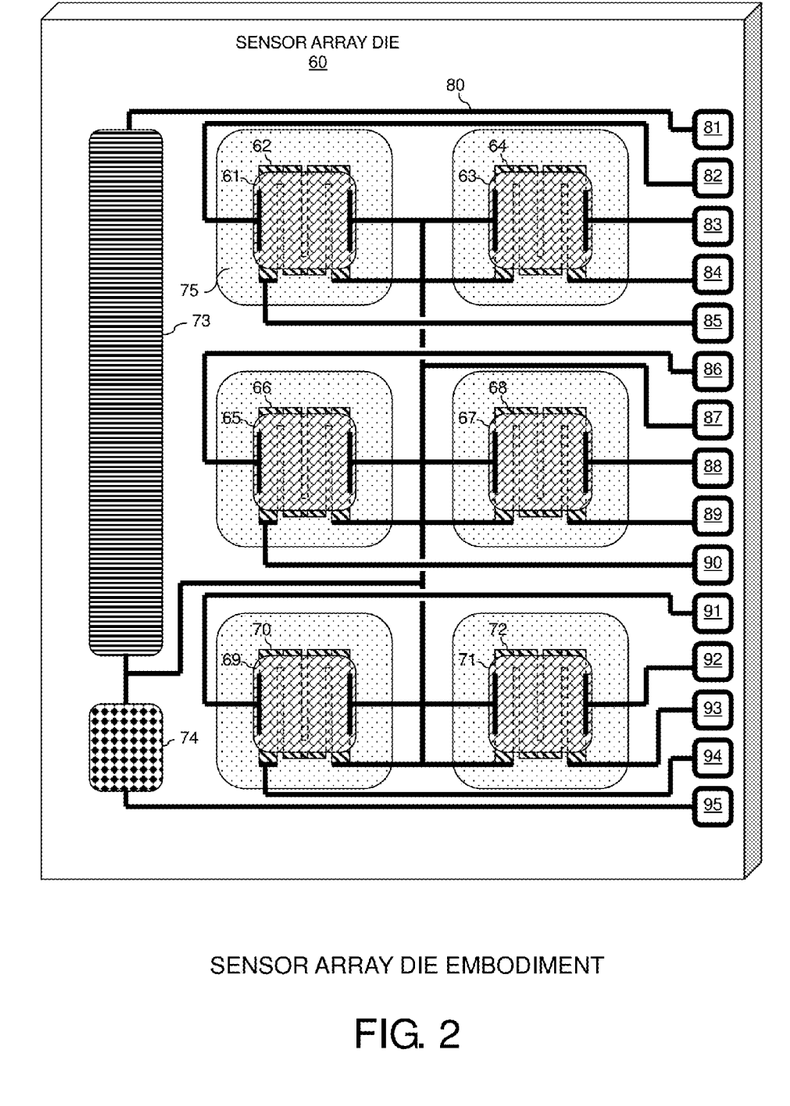
FIG. 2 is an exemplary diagram of a sensor array in a two-die embodiment of the OACIC.

FIG. 2 is an exemplary diagram of a sensor array die 60 in a two-die embodiment of the OACIC. For example, the sensor array 2 shown in FIG. 1 is disposed on the sensor array die 60. Sensor array die 60 comprises six gas sensors with their associated heating resistors, a humidity sensor 73 and an ambient temperature sensor 74. Sensor 61 is heated by heating resistor 62 below it. Sensor 63 is heated by heating resistor 64 below it. Sensor 65 is heated by heating resistor 66 below it. Sensor 67 is heated by heating resistor 68 below it. Sensor 69 is heated by heating resistor 70 below it. Sensor 71 is heated by heating resistor 72 below it. Each gas sensor and heating resistor pair is positioned atop a micro-machined cavity 75 that thermally isolates the gas sensor and heating resistor from the silicon substrate. Each gas sensor can be heated to a different individual temperature by its own heating resistor. In another embodiment, a membrane made of silicon nitride provides further thermal isolation between the gas sensor and heating resistor and the silicon substrate. The micro-machined cavity 75 is formed by either wet etching or dry etching of the bulk silicon material. The terminals of the gas sensors, the heating resistors, humidity sensor 73, and ambient temperature sensor 74 are routed with conducting material 80 to bonding pads 81 to 95 for bonding to a mixed signal die. The bonding pads are lined up on one edge of the sensor array die 60 to facilitate bonding to another die.

In an embodiment of the present invention, the sensor array die 60 uses the same heating resistors for heating and temperature sensing of the gas sensors. The heating resistors are typically fabricated as poly-silicon resistors with a temperature coefficient. During the heating, a pulse-width-modulated voltage pulse drive signal is applied across each heating resistor to control the amount of heating power. The current through each heating resistor is used to determine its temperature. In other embodiments, each sensor in the sensor array die is associated with a heating resistor and a separate temperature sensing resistor.

Figure 3:
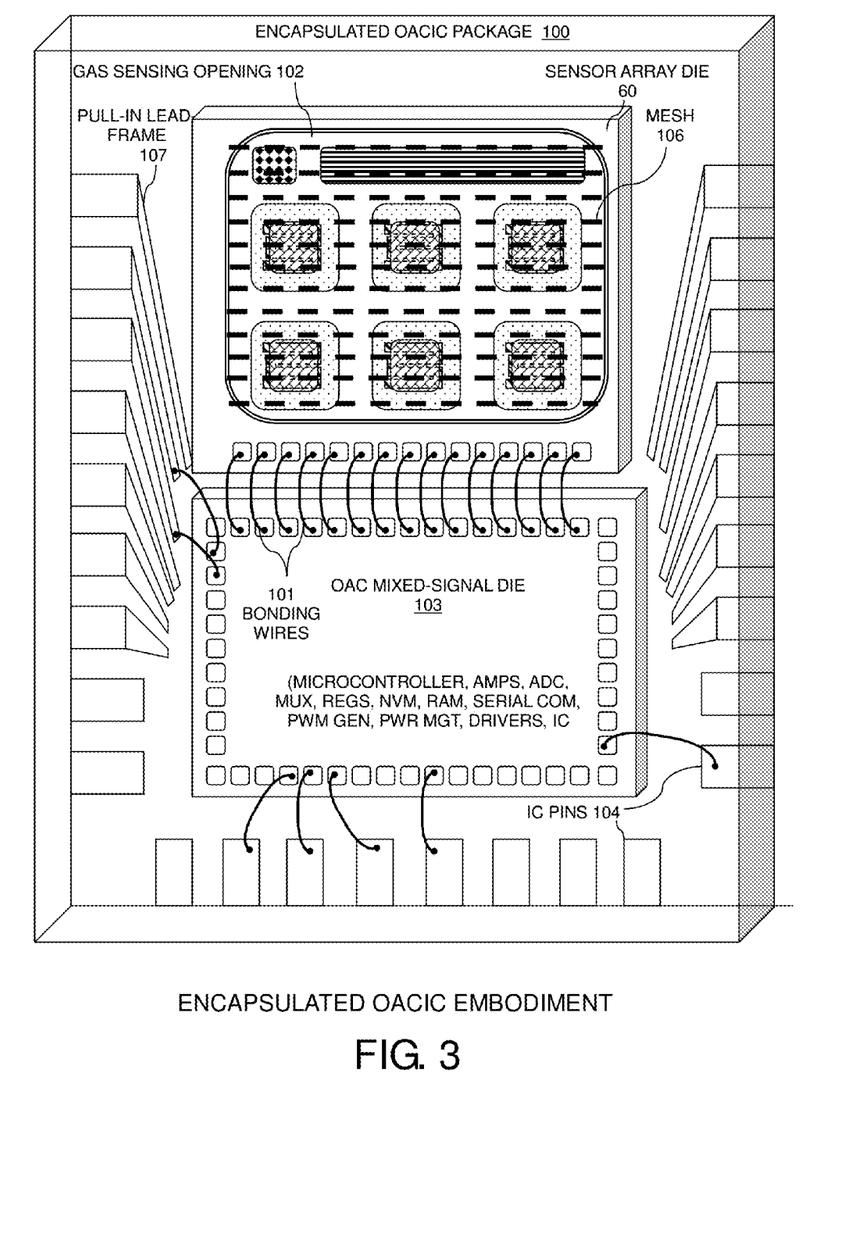
FIG. 3 is an exemplary simplified diagram of an encapsulated OACIC embodiment.

FIG. 3 is an exemplary simplified diagram of an encapsulated OACIC embodiment. Encapsulated OACIC package 100 includes sensor array die 60 and OAC mixed-signal die 103. Sensor array die 60 includes gas sensors 10, heating resistors 11, a humidity sensor 13, and an ambient temperature sensor 14 as shown in FIG. 1. OAC mixed-signal die 103 includes amplifiers 3, a multiplexer 4, a humidity and ambient temperature converter 28, an analog-to-digital converter (ADC) 5, a pulse-width-modulation (PWM) generator 6, heater drivers 7, a result register 8, a microcontroller 9, a nonvolatile memory 27, a random-access memory (RAM) and register 20, a digital comparator 25, an alarm register 23, an auto-scan circuit 26, a serial communication circuit 21, and a power management circuit 22 as shown in FIG. 1. Sensor array die 60 and OAC mixed-signal die 103 are connected to each other with bonding wires 101. Encapsulated OACIC package 100 has a gas sensing opening 102 for gas molecules to enter and interact with the sensing materials and sensing devices in the sensory array die 60. The gas sensing opening 102 may be covered with a mesh 106 to prevent large pollutant particles from entering the gas sensing opening 102 and covering the sensors. Since the sensor array die 60 takes up a large portion of the package, the encapsulated OACIC package 100 uses a pull-in lead-frame 107 to bring the pins near the sensor array die 60 closer to the OAC mixed-signal die 103 for bonding to its pads. The ports in the OAC mixed-signal die 103 are wire-bonded to IC pins 104 on the encapsulated OACIC package 100 for connection to external signals and devices.

Figure 4:
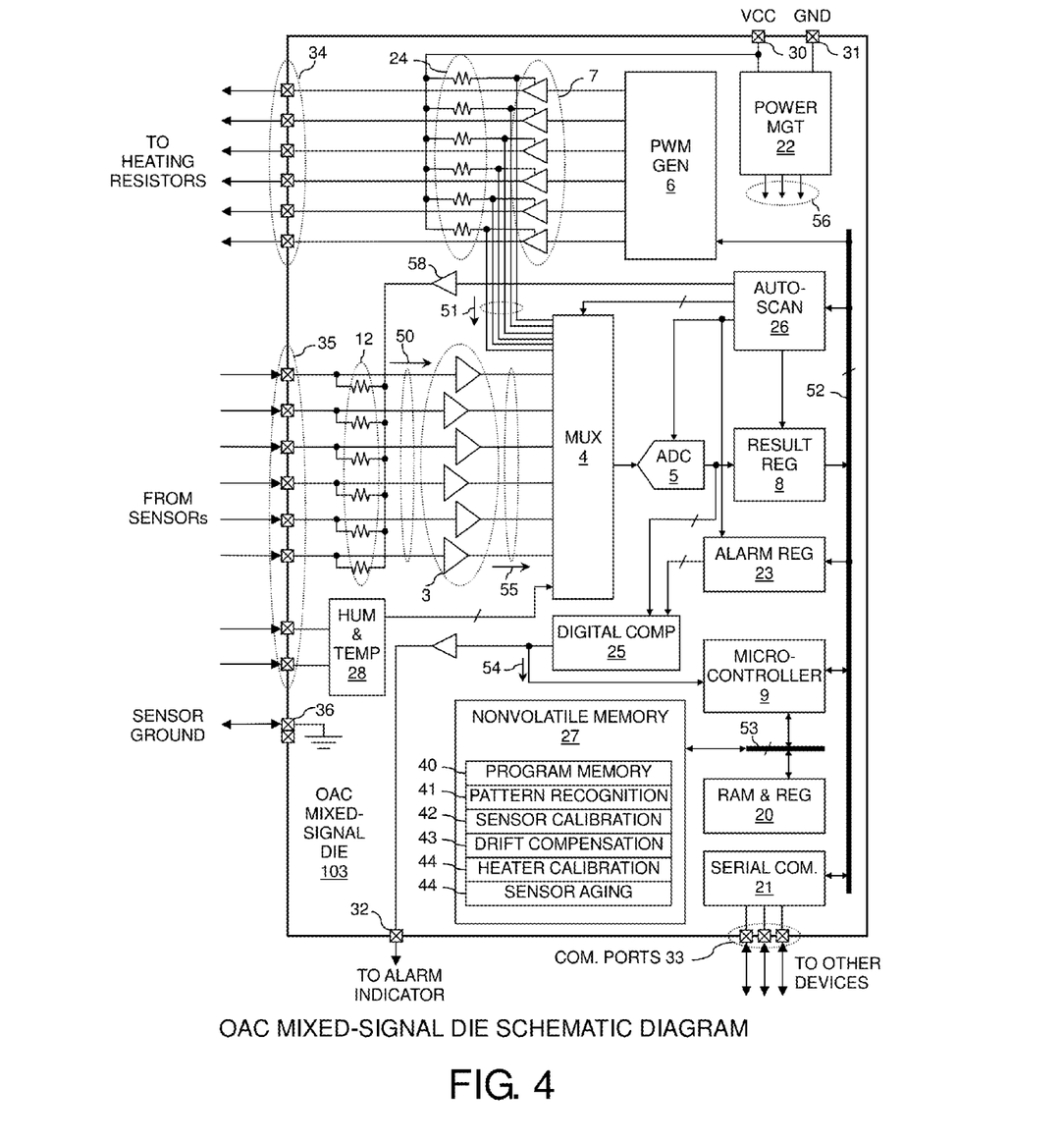
FIG. 4 is an exemplary schematic diagram of a mixed-signal OAC in a two-die embodiment of the OACIC.

FIG. 4 is an exemplary schematic diagram of the OAC mixed-signal die 103 in a two-die embodiment of the OACIC. The OAC mixed-signal die 103 includes all the circuitry block of OACIC 1 in FIG. 1 except for sensor array 2 (as embodied in the sensor array die 60 of FIG. 2). The OAC mixed-signal die includes bond pads 34 for bonding to the heating resistors in the sensor array die 60, as well as bond pads 35 for bonding to the sensors in the sensor array die 60. The OAC mixed-signal die further includes supply bond pads such as ground bond pads 36 to provide a ground supply to the sensor array die 60.

Figure 5:
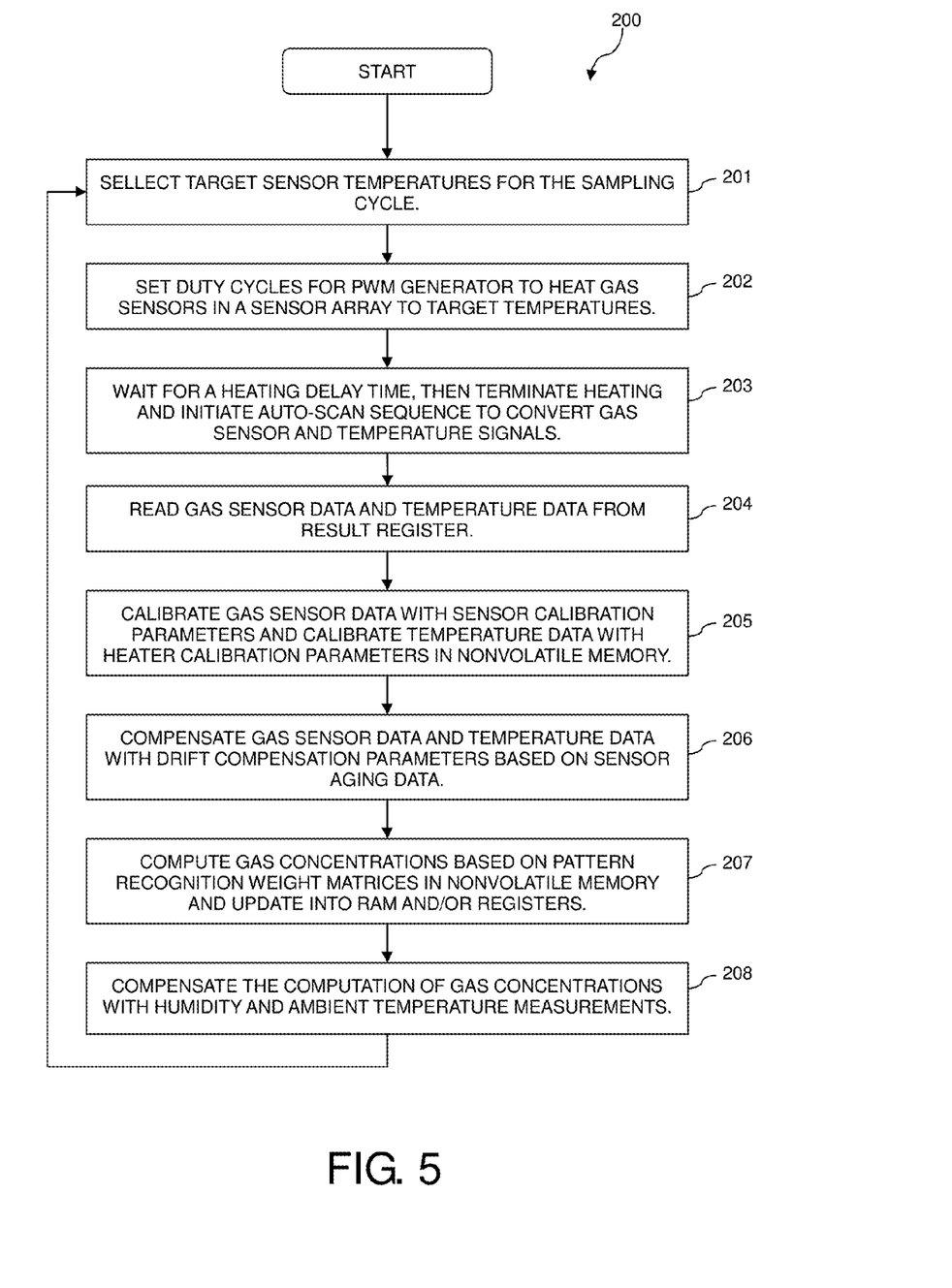
FIG. 5 is an exemplary method for measuring gas concentrations using the OACIC.

FIG. 5 is an exemplary method 200 for measuring gas concentrations using the OACIC 1 of FIG. 1. In a first step (201), the OACIC selects the target sensor temperatures for the sampling cycle. Each gas sensor can have a different individual target temperature. For increased selectivity and detection of different gases, the temperatures can be different for each sampling cycle. For example, two consecutive sampling cycles may use two different temperature vectors to double the data size for pattern recognition. The temperature vectors are preprogrammed in the algorithm in the nonvolatile memory. In a second step (202), the OACIC sets the duty cycles for the PWM generator to heat the gas sensors in the sensor array to target temperatures. In a third step (203), the OACIC waits for a heating delay time, then disables the PWM generator to terminate the heating and initiates an auto-scan sequence to convert the gas sensor and temperature signals from the sensor array into sensor data and temperature data in the result register. In a fourth step (204), the OACIC reads gas sensor data and temperature data from the result register. In a fifth step (205), the OACIC calibrates the gas sensor data with the sensor calibration parameters and calibrates the temperature data with the heater calibration parameters in the nonvolatile memory. In a sixth step (206), the OACIC compensates the gas sensor data and the temperature data with drift compensation parameters based on sensor aging data. In a seventh step (207), the OACIC computes gas concentrations based on pattern recognition weight matrices in nonvolatile memory and updates the gas concentrations into the RAM and/or registers of the OACIC. In an eighth step (208), the OACIC compensates the computation of gas concentrations with humidity and ambient temperature measurements. The period between sampling cycles is based on the gas concentrations so that the OACIC samples less frequently for higher gas concentrations in order to minimize aging effect caused by high gas concentrations. For abnormally high gas concentrations, the OACIC can disable sampling to protect the sensors until the OACIC is powered down or cleared by a command through serial communication.

Figure 6:
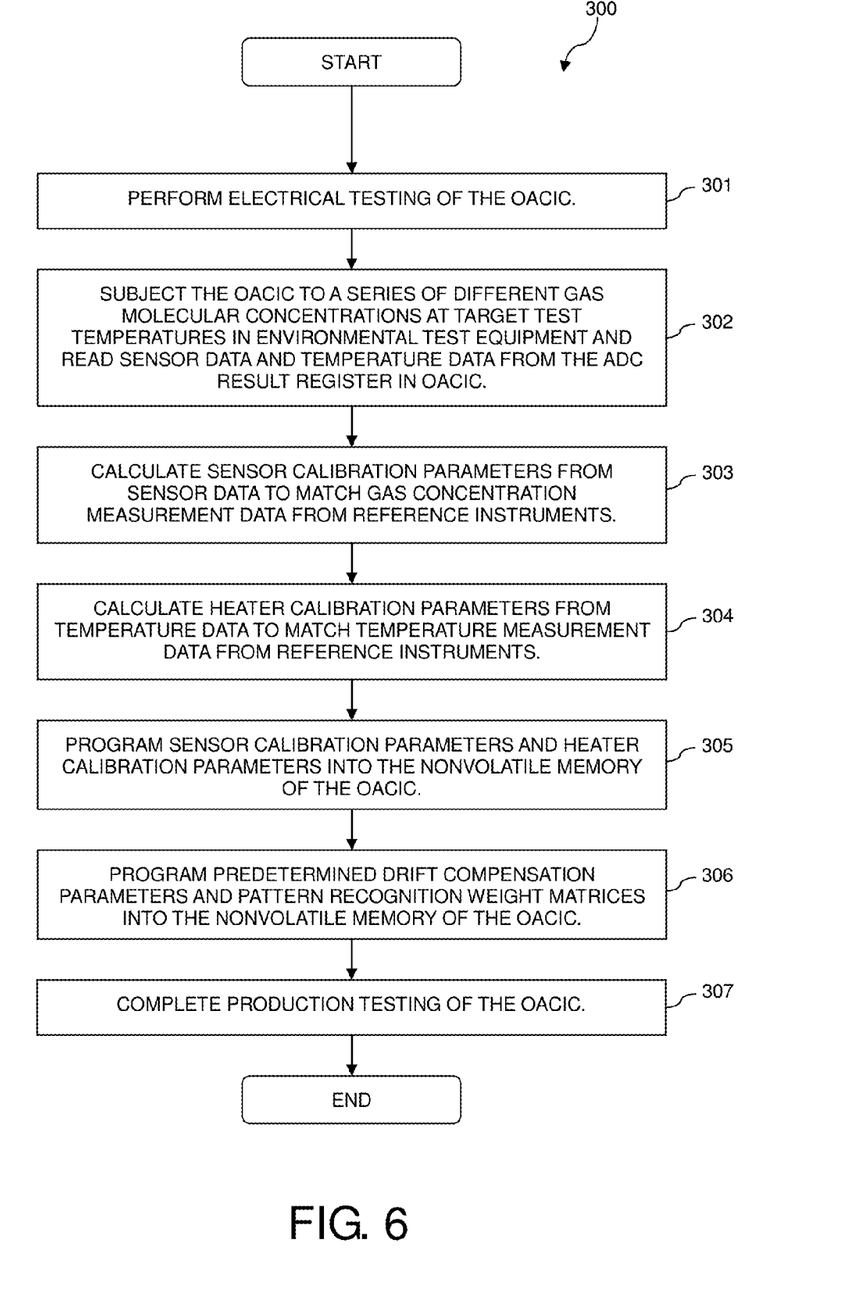
FIG. 6 is an exemplary method for mass production and calibration of the OACIC.

FIG. 6 is an exemplary method 300 for mass producing the OACIC 1 of FIG. 1. In a first step (301), the electrical testing of the OACIC is performed. In a second step (302), the OACIC is subjected to a series of different gas molecular concentrations at target test temperatures in environmental test equipment. The sensor data and temperature data in the OACIC result register is then read. In a third step (303), the sensor calibration parameters are calculated from the sensor data to match gas concentration measurement data from reference instruments. In a fourth step (304), the heater calibration parameters are calculated from the temperature data to match temperature measurement data from reference instruments. In a fifth step (305), the sensor calibration parameters and heater calibration parameters are programmed into the nonvolatile memory of the OACIC. In a sixth step (306), the drift compensation parameters and pattern recognition weight matrices are programmed into the nonvolatile memory of the OACIC. In a seventh step (307), the production testing of the OACIC is performed. Method 300 allows the OACIC to be calibrated at the factory during mass production so that users do not need to calibrate for the gas concentration measurements after assembling the OACIC into end devices and equipment.

Figure 7:
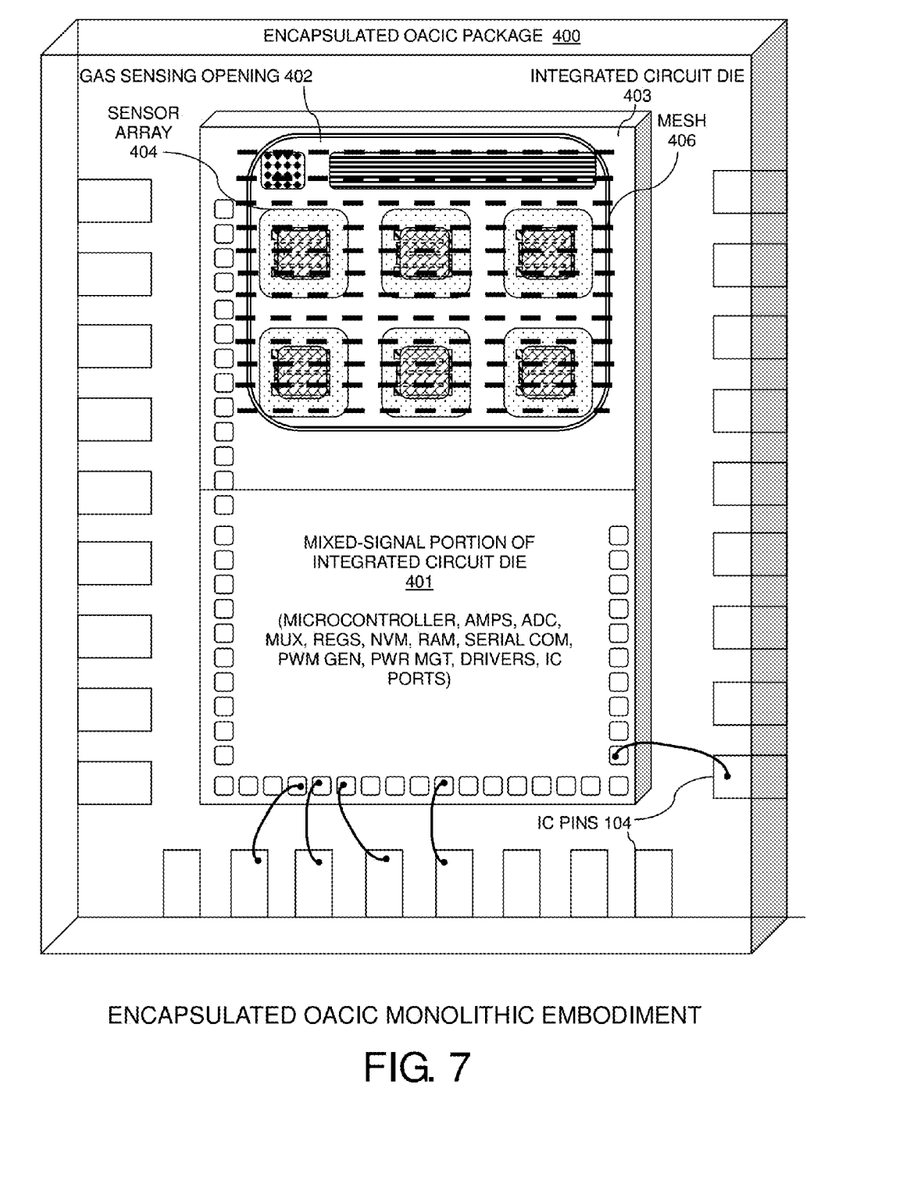
FIG. 7 is an exemplary simplified diagram of an encapsulated OACIC.

FIG. 7 is an exemplary simplified diagram of an encapsulated OACIC. In this embodiment, a single integrated circuit die 403 includes both the sensor array 404 and the mixed-signal portion of the integrated circuit die 401. The integrated circuit die 403 is encapsulated in an encapsulated OACIC package 400 having a gas sensing opening 402 that is covered by a mesh 406.

The integrated ambient temperature and humidity sensor in the sensor array 404 not only provides environment readings for system control, but also enables on-chip metal oxide semiconductor (MOX) sensor calibration to eliminate the impacts caused by surrounding temperature and humidity changes on the sensor's sensitivity. The sensor array 404 allows individual sensor cells to be set at different temperatures. Different optimized material compositions for each gas sensor cell enable the sensors to identify target gases with more accuracy by mitigating sensor cross-sensitivity. Long-term drift of sensitivity can be corrected with the microcontroller field-programmable algorithm in the OACIC. The OACIC is programmed to issue warning of possible contamination of the device. Embedded processing and smart control enable self-protection of the sensor array 404 by shutting it off when gas concentration is abnormal.

Although certain specific embodiments are described above for instructional purposes, the teachings of this patent document have general applicability and are not limited to the specific embodiments described above. For example, different materials, compositions, and micro-machined structures may be used for the construction of the sensor arrays. The sensors may operate with different sensing mechanisms, and may provide other types of signals besides voltage or current signals. For additional information on the structure and operation of the OACIC, see: U.S. Provisional Application Ser. No. 61/990,705, entitled "Olfactory Application Controller Integrated Circuit," filed May 8, 2014, by Huynh et al. (the entire subject matter of which is incorporated herein by reference).

Accordingly, various modifications, adaptations, and combinations of various features of the described embodiments can be practiced without departing from the scope of the invention as set forth in the claims.

What is claimed is:

1. An integrated circuit, comprising:
a microcontroller;
a nonvolatile memory;
a set of at least two gas sensors, wherein the gas sensors are exposed to air, wherein each gas sensor has an attribute, wherein the attribute of each gas sensor has a different dependency on a gas concentration;
a set of heating resistors, wherein each heating resistor is associated with an associated gas sensor, wherein each heating resistor raises the temperature of the associated gas sensor to a target temperature;
an analog-to-digital converter operable to convert the attributes of the gas sensors into digital values, wherein the digital values corresponding to at least two gas sensors are used by the microcontroller to compute the gas concentration, wherein the at least two gas sensors are differentially sensitive to the gas concentration; and
a communication circuit operable to communicate the gas concentration information out of the integrated circuit.

2. The integrated circuit of claim 1, further comprising a humidity sensor and an ambient temperature sensor, wherein information from the humidity sensor and ambient temperature sensor are used in computing the gas concentration.

3. The integrated circuit of claim 1, wherein the integrated circuit is field programmable.

4. The integrated circuit of claim 1, wherein the integrated circuit is encapsulated in a plastic package with an opening for gas molecules to enter and interact with the gas sensors.

5. An integrated circuit, comprising:
a microcontroller;
a nonvolatile memory;
a set of at least two gas sensors, wherein the gas sensors are exposed to air, wherein each gas sensor has an attribute, wherein the attribute of each gas sensor has a different dependency on a gas concentration;
a set of heating resistors, wherein each heating resistor is associated with an associated gas sensor, wherein each heating resistor raises the temperature of the associated gas sensor to a target temperature;
an analog-to-digital converter operable to convert the attributes of the gas sensors into digital values, wherein the digital values corresponding to at least two gas sensors are used by the microcontroller to compute the gas concentration, wherein the at least two gas sensors are differentially sensitive to the gas concentration; and
a communication circuit operable to communicate the gas concentration information out of the integrated circuit, and wherein the nonvolatile memory stores sensor calibration parameters.

6. An integrated circuit, comprising:
a microcontroller;
a nonvolatile memory;
a set of at least two gas sensors, wherein the gas sensors are exposed to air, wherein each gas sensor has an attribute, wherein the attribute of each gas sensor has a different dependency on a gas concentration;
a set of heating resistors, wherein each heating resistor is associated with an associated gas sensor, wherein each heating resistor raises the temperature of the associated gas sensor to a target temperature;
an analog-to-digital converter operable to convert the attributes of the gas sensors into digital values, wherein the digital values corresponding to at least two gas sensors are used by the microcontroller to compute the gas concentration, wherein the at least two gas sensors are differentially sensitive to the gas concentration; and
a communication circuit operable to communicate the gas concentration information out of the integrated circuit, and wherein the nonvolatile memory stores pattern recognition weight matrices for computing the gas concentration.

7. An integrated circuit, comprising:
a microcontroller;
a nonvolatile memory;
a set of at least two gas sensors, wherein the gas sensors are exposed to air, wherein each gas sensor has an attribute, wherein the attribute of each gas sensor has a different dependency on a gas concentration;
a set of heating resistors, wherein each heating resistor is associated with an associated gas sensor, wherein each heating resistor raises the temperature of the associated gas sensor to a target temperature;
an analog-to-digital converter operable to convert the attributes of the gas sensors into digital values, wherein the digital values corresponding to at least two gas sensors are used by the microcontroller to compute the gas concentration, wherein the at least two gas sensors are differentially sensitive to the gas concentration; and
a communication circuit operable to communicate the gas concentration information out of the integrated circuit, and wherein the integrated circuit computes the gas concentration with data from at least one gas sensor at two different temperatures.

8. The integrated circuit of claim 7, wherein each heating resistor is driven by a driving signal having a pulse-width-modulation duty cycle, wherein the pulse-width-modulation duty cycle is controlled by the microcontroller to set the heating resistor to a target temperature.

9. The integrated circuit of claim 7, wherein the integrated circuit does not drive the heating resistors to produce heat when an abnormal gas concentration or humidity is detected.

10. The integrated circuit of claim 7, further comprising an auto-scan circuit to sequentially convert the attributes of the gas sensors into digital values and store the digital values into a result register.

11. An apparatus comprising:
a first gas sensor that measures a first attribute of a gas concentration;
a second gas sensor that measures a second attribute of the gas concentration, wherein the first attribute varies with the gas concentration differently than does the second attribute, and wherein the first gas sensor and the second gas sensor are differently sensitive to the gas concentration;
a first heating resistor that sets a temperature of the first gas sensor to a first target temperature;
a second heating resistor that sets a temperature of the second gas sensor to a second target temperature; and
an analog-to-digital converter that converts the attributes measured by the first gas sensor and the second gas sensor into digital values that are used to compute the gas concentration.

12. The apparatus of claim 11, wherein the first heating resistor is driven with a signal having a pulse-width-modulation duty cycle, wherein the pulse-width-modulation duty cycle is controlled to set the first heating resistor to the first target temperature.

13. The apparatus of claim 11, further comprising:
a humidity sensor; and
an ambient temperature sensor, wherein information from the humidity sensor and the ambient temperature sensor is used to compute the gas concentration.

14. The apparatus of claim 11, wherein the apparatus is field programmable device.

15. The apparatus of claim 11, further comprising:
a nonvolatile memory that stores sensor calibration parameters.

16. The apparatus of claim 15, wherein the nonvolatile memory stores pattern recognition weight matrices that are used to compute the gas concentration.

17. The apparatus of claim 11, wherein the integrated circuit is encapsulated in a plastic package with an opening for gas molecules to enter and interact with the first and second gas sensors.

18. A method comprising:
driving a first signal through a heating resistor thermally coupled to a gas sensor;
raising the temperature of the gas sensor to a target temperature by adjusting a duty cycle of the first signal;
generating a temperature signal indicative of the temperature of the gas sensor;
generating a sensor signal indicative of a gas concentration at the gas sensor;
converting the temperature signal into temperature data;
converting the sensor signal into sensor data;
calibrating the sensor data and the temperature data;
storing the sensor data and the temperature data in a nonvolatile memory;
generating pattern recognition weight matrices by running pattern recognition learning algorithms on the sensor data and the temperature data stored in the nonvolatile memory; and
computing a value of the gas concentration using the pattern recognition weight matrices.

19. The method of claim 18, further comprising:
adjusting the value of the gas concentration based on humidity and ambient temperature measurements.

20. The method of claim 18, further comprising:
adjusting the sensor data based on an age of the gas sensor.

* * * * *